United States Patent [19]

Braunstein et al.

[11] Patent Number: 4,609,639

[45] Date of Patent: Sep. 2, 1986

[54] HETEROPOLYMETALLIC CLUSTERS, METHODS OF MAKING SUCH CLUSTERS, AND CATALYSTS UTILIZING SUCH CLUSTERS

[75] Inventors: Pierre Braunstein, Strasbourg; Jacques Kervennal, Lyon; Jean-Luc Richert, Schiltigheim; Michel Ries, Strasbourg, all of France

[73] Assignee: ATOCHEM, France

[21] Appl. No.: 691,453

[22] Filed: Jan. 14, 1985

[30] Foreign Application Priority Data

Jan. 17, 1984 [FR] France ............................. 84 00630

[51] Int. Cl.$^4$ ............................................ B01J 23/89
[52] U.S. Cl. ..................................... 502/326; 556/14
[58] Field of Search ............................. 502/326, 327; 260/429 R; 556/14

[56] References Cited

U.S. PATENT DOCUMENTS 2,857,337 10/1958 Hamilton et al. .................. 502/326

FOREIGN PATENT DOCUMENTS 56-169636 12/1981 Japan .................................. 502/326

Primary Examiner—W. J. Shine
Attorney, Agent, or Firm—Sigalos & Levine

[57] ABSTRACT

Heteropolymetallic clusters of the formula $Pd_2(Fe)_x(CO)_4[Co(NO)_2]_y[bis(diphenylphosphine)methane]_2$ wherein x is 1 or 2 and y is 0 or 1; x=2 when y=1 and x=1 when y=0; to the method of making such clusters by reacting $Pd_2Cl_2[bis(diphenylphosphine)methane]$ with $MnFe(CO)_3Z$ wherein M is an alkaline metal and Z is CO (n=2) or NO (n=1); and to the novel catalysts formed utilizing said clusters.

10 Claims, No Drawings

HETEROPOLYMETALLIC CLUSTERS, METHODS OF MAKING SUCH CLUSTERS, AND CATALYSTS UTILIZING SUCH CLUSTERS

BACKGROUND OF THE INVENTION

The present invention concerns new heteropolymetallic clusters containing palladium and iron, their synthesis, and catalysts made utilizing the clusters.

As used herein, the term "clusters" means molecular structures comprising at least three metallic atoms connected to one another by metal-metal bonds, with these structures possessing ligands which, by their structure, more or less stabilize them. Such kinds of clusters are especially advantageous in preparing catalysts by impregnating them on a support, followed by thermal treatment and reduction in order to obtain metallic particles.

Mixed complexes of the general formula:

$$Pd_2(Fe)_x(CO)_4[CO(NO)_2]_y(dppm)_2$$

with $x=2$ when $y=1$ and $x=1$ when $y=0$; "dppm" designating the ligand bis(diphenylphosphino)methane, can thus be considered as clusters in conformity with this invention.

The association of iron and palladium permits obtaining interesting results in certain catalytic reactions and it is then important that the distribution and the dispersion of the metals be the best possible. In the case of bi-metallic catalysts containing supported iron, the structure of the catalyst and the state of the valence of the metals are obviously primordial. C. H. BARTHOLOMEW and M. BOUDART have shown in the JOURNAL OF CATALYSIS, 29, 278 (1973) that the stages of impregnation, of heat treatment, and of reduction, as well as the nature of the support, are very important in order to obtain highly dispersed catalysts. In fact, if the metal/support interaction is weak, the metallic particles produced can easily migrate to the surface and form large crystallites thus on silica, if one prepares a catalyst by impregnation of an aqueous ferric nitrate solution, the metal/support interaction is weak and leads to large crystallites, of a mean size of 15 μm, as L. GUCZI and coworkers have shown in the JOURNAL OF CATALYSIS, 60, 121 (1979) and R. L. GARTEN in MOSSBAUER EFF. METHOD, 10, 69 (1977). The fact of starting out from metallic salts in aqueous solutions makes the pH phenomena important which affects the interaction between the surface and the ion and can lead to precipitations at the surface. The metal/support interaction is much more important in the case of alumina as shown by R. L. GARTEN and D. F. OLLIS in the JOURNAL OF CATALYSIS, 35, 232 (1974) and one can prepare a highly dispersed catalyst. On the other hand, by starting from Fe (III), the reduction into Fe (O) cannot be totally effected. One possibility of producing a catalyst in which the iron is highly dispersed and in a state of oxidation near O thus is to deposit iron of low valence on the support. This can be achieved by using carbonyl metals as shown by A. BRENNER in the JOURNAL OF MOLECULAR CATALYSIS, 5, 157 (1979) in J. M. BASSET and R. UGO in ASPECTS OF HOMOGENEOUS CATALYSIS, vol. II, 137, Reidel (1976). In the case in which one searches for bi-metallic catalysts, one sees the advantage one has by starting from heteropolynuclear types such as mixed clusters in which the ligands bestow low oxidation states on the metals. In fact, conventional bi-metallic catalysts are prepared by impregnation with an aqueous salt solution. The impregnations of salts can, moreover, be simultaneous or successive, but there again modifications of the pH during the course of impregnation can provoke processes of metallic aggregation and thus a poor dispersion of phases. In addition, the adsorption velocities generally are not identical and in the event that impregnation takes place on pre-formed supports, concentration gradients appear which are different for the two metals.

These drawbacks disappear with bi-metallic molecular clusters probably because they conduct to well-dispersed and uniform heterometallic phases, with the impregnated clusters capable of keeping the geometry of the starting complexes. The formation of bi-metallic surface aggregates from standard impregnations of derivatives of platinum or palladium and of iron has, however, been noted and described by J. J. BURTON and R. L. GARTEN in ADVANCED MATERIALS IN CATALYSIS, Academic, New York, 33 (1977). But in this case one is not master of the stoichiometry of the types formed. On the contrary, the fact of starting with molecular complexes in which the metal-metal bonds are stable makes it possible to better control the arrangements formed and their stoichiometry.

Very few molecular structures containing palladium-iron bonds have been characterized to the present day. There can be cited the complex of $[FePd(\mu Cl)(\mu PPh_2)(CO_4]_2$ prepared by B. C. BENSON, R. JACKSON, K. K. JOSHI, and D. T. THOMPSON after their description in CHEMICAL COMMUNICATIONS, 1506 (1968), as well as the types $[Fe_4Pd(CO)_{16}]^{2-}$, $[Fe_6Pd_6H(CO)_{24}]^{3-}$, and $[Fe_6Pd_6(CO)_{24}]^{4-}$ described by G. LONGONI, M. MANASSERO, and M. SANSONI in the JOURNAL OF THE AMERICAN CHEMICAL SOCIETY, vol. 102, 3242 (1980). In fact, only the three last complexes respond to the definition of clusters given at the start of this description and possess palladium-iron bonds stabilizing the molecular structure, but it should be noted that we are dealing with ionic types. This factor can hurt or complicate their eventual use as catalysts or precursors of catalysts, because one cannot avoid the simultaneous introduction of the corresponding counter-ion, which results in involving a supplementary parameter from which one cannot be freed.

SUMMARY OF THE INVENTION

Outside of the fact of being neutral, the instant claimed clusters present the advantage of possessing diphosphine ligands which, by their bidentate character, reinforce the solidity of the structures.

Briefly, the present invention comprises a heteropolymetallic cluster of the formula $Pd_2(Fe)_x(CO)_4[CO(NO)_2]_y[bis(diphenylphosphine)methane]_2$ wherein x is 1 or 2 and y is 0 or 1; $x=2$ when $y=1$ and $x=1$ when $y=0$; to the method of making such clusters by reacting $Pd_2Cl_2[bis(diphenylphosphine)methane]$ with $M_nFe(CO)_3Z$ wherein M is an alkaline metal and Z is CO ($n=2$) or NO ($n=1$); and to the novel catalysts formed utilizing said clusters as hereinafter described.

DETAILED DESCRIPTION

The synthesis of the clusters of the invention calls on several reaction stages. Thus, for the palladium, the complex $PdCl_2(PhCN)_2$ is prepared by the reaction of PdCl₂ and benzonitrile as described by F. A. HARTLEY in ORGANOMETAL CHEM. REV. 6, 119 (1970) and the complex Pd₂(dba)₃, CHCl₃ (dba: dibenzylideneacetone) by the reaction of PdCl₂ and of dibenzylidene acetone as described by T. UKAI, H. KAWAZURA, Y. ISHII, J. BONNET, J. A. IBERS in J. ORGANOMET, CHEM. 65, 253 (1974). The placement into reaction of these two types in the presence of bis(diphenylphosphino)methane (dppm) according to the equation:

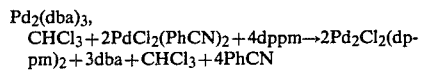

Pd₂(dba)₃,
CHCl₃+2PdCl₂(PhCN)₂+4dppm→2Pd₂Cl₂(dppm)₂+3dba+CHCl₃+4PhCN (see L. S. BENNER and A. L. BALCH, J. AMER. CHEM. SOC., 100, 6099 (1978)).

This complex is used as precursor in order to synthesize the clusters of the invention by causing it to react with a compound $M_nFe(CO)_3Z$, with M being an alkaline metal and Z is CO or NO. Thus, KFe(CO)₃NO which can be prepared from Fe(CO)₅ and KNO₂ as described by W. HIEBER and H. BEUTNER in Z. NATURFORSCH. Col. 15B, 323 (1960), and Na₂Fe(CO)₄ described by J. P. COLLMAN and colleagues in the J. AMER. CHEM. SOC. 94, 1788 (1972) and in ACCOUNTS CHEM. RES., vol. 8, 342 (1975) can react with Pd₂Cl₂(dppm)₂ in order to lead respectively to the two types: Pd₂Fe₂(dppm)₂(CO)₅(NO)₂ and Pd₂Fe(CO)₄(dppm)₂. One can note that these two complexes make it possible to cause the atomic ratio of Pd/Fe to vary. The reaction usually takes place in the presence of inert solvents such as, for instance, tetrahydrofuran (THF) or dioxane at temperatures of 0° C. or below.

It has been possible to determine the structure of the clusters on analytical and spectroscopic bases:

(a) Pd₂Fe₂(dppm)₂(CO)₅(NO)₂: The elementary analysis is in conformity with this general formula and the nuclear magnetic resonance (N.M.R.) data likewise confirm a mixed tetrametallic complex having two palladium atoms and two iron atoms and presenting a triangular geometry:

| N.M.R. ¹H (CDCl₃) | |
|---|---|
| = 7.7–6.8 ppm | multiplet of 40 aromatic protons of bis(diphenylphosphino) methane |
| = 4.50 ppm | "doublet of triplets" corresponding to two protons of CH₂ |
| = 3.91 ppm | "triplet" corresponding to two protons of CH₂ |
| N.M.R. ³¹P (CDCl₃ - reference: H₃PO₄ 85%) | |
| = +40 ppm | multiplet corresponding to one atom of phosphorus |
| = +4.6 to −9.1 ppm | unit of 22 lines, corresponding to 3 atoms of phosphorus |

As a first analysis, the N.M.R. of the proton at the level of the methylene groups shows a triplet due to the CH₂ of the dppm ligand bridging the Pd-Pd bond and a doublet of triplet, at lower field, due to the CH₂ bridging the Pd-Fe bond which is coupled to a P of an adjacent bridge.

The N.M.R. of the ³¹P confirms a triangular structure showing 1 atom of phosphorus linked to one atom of Fe and very different from the three other P (atoms) linked to the palladium atoms. This leads to attributing the following structure to the cluster:

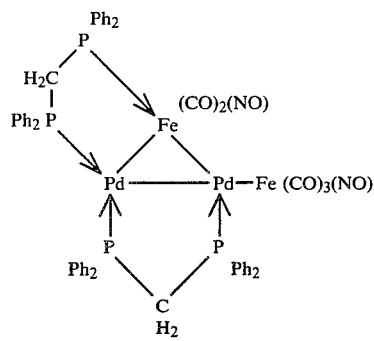

(b) Pd₂Fe(CO)₄(dppm)₂: The elementary analysis is in conformity with this general formula, with the N.M.R. spectra suggesting a mixed trimetallic complex of triangular geometry:

| N.M.R. ¹H (CD₂Cl₂) | |
|---|---|
| δ = 7.5–6.4 ppm | multiplet of 40 aromatic protons of bis(diphenylphosphino) methane |
| δ = 4.4 ppm | center of a pattern of triplet aspect corresponding to two protons of CH₂ |
| δ = 4.2 ppm | center of a second pattern of triplet aspect corresponding to two protons of CH₂ |
| N.M.R. ³¹P (CD₂Cl₂ - reference: H₃PO₄ 85%) | |
| = +54.3 ppm | center of a pattern of 6 lines corresponding to 1 atom of phosphorus |
| = −2.9 to −8.6 ppm | pattern of 15 lines corresponding to 3 atoms of phosphorus. |

These results permit attributing the following structure to the cluster:

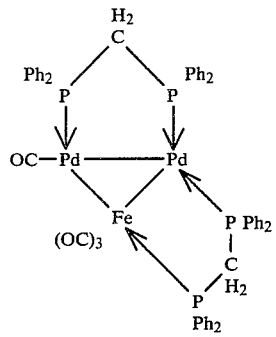

The supports which can be utilized in order to prepare the catalysts are those conventionally used for catalysts; preferably aluminas, silica-aluminas, silicas, charcoals, molybdenum oxide, and the like. The catalysts can be prepared by any conventional process, including the following stages:
(i) impregnation of the support with a solution of the cluster in an organic solvent;
(ii) drying the impregnated support and heating; and
(iii) reduction at the end of the thermal treatment in order to liberate the metallic particles.

The impregnation of the supports was carried out in a rotary evaporator. The solution of the cluster is either added onto the support in one stage and the solvent expelled under reduced pressure or introduced slowly onto the support in such a way as to deposit on the support a quantity of palladium between 0.1 and 10% by weight, with the iron being present at a percentage by weight corresponding to the stoichiometry of the cluster. The thermal treatment can be carried out by heating under a nitrogen current of 20° C. up to a temperature between 450° and 500° C. by means of temperature programming, followed by a temperature plateau of several hours, about 10 to 30, at the final temperature, a sweeping with hydrogen being admitted at the end of the plateau.

Set forth below is a non-limiting illustrative example of application of such a catalyst to the carbonylation of ortho nitrophenol in benzoxazolone-2.

For the sake of precaution, the manipulations of the complexes are carried out under nitrogen or argon and the solvents are dried and distilled.

The invention will be further described in connection with the following examples which are set forth for purposes of illustration only.

EXAMPLE 1

A solution of $KFe(CO)_3NO$ (2.8 g, 13.4 mmoles), prepared according to the description made by W. HIEBER and H. BEUTNER in Z. NATURFORSCH. vol. 15B, 323 (1960) in 500 ml of THF is added dropwise to a suspension of $Pd_2(dppm)_2Cl_2$ (6.46 g; 6.1 mmoles), whose synthesis has been described by L. S. BENNER and A. L. BALCH in J. AMER. CHEM. SOC., 100, 6099 (1978) and placed into 500 ml of THF at −78° C. The mixture is protected from light. The temperature is allowed to rise to 0° C.; the mixture progressively passes from orange to dark red, then to violet at the end of three hours. The mixture is then allowed to come to ambient temperature, while maintaining agitation until the coloration is green.

The reaction mixture is filtered on fritted glass in order to eliminate KCl, decomposition products and $Pd_2(dppm)_2(\mu CO)Cl_2$ which has formed. The dark green filtrate is concentrated and made to precipitate with hexane. There is thus recovered 5.04 g of dark green solid (yield 64% based on Pd) recrystallizable in the $CHCl_2$/hexane mixture.

Elementary analysis: theoretical: $C=51.07\%$; $H=3.43\%$; $N=2.16\%$. found: $C=50.6\%$; $H=3.75\%$; $N=1.91\%$.

Infra-red bands:
(KBr pellet):
1974 $cm^{-1}$ (intense);
1880 $cm^{-1}$ (intense, large);
1840 $cm^{-1}$ (shoulder);
1736 $cm^{-1}$ (intense);
1683 $cm^{-1}$ (intense).
melting point=178° C. (decomposition)

The analysis and N.M.R. data lead to attributing the formula $Pd_2Fe_{2L\ (dppm)2}(CO)_5(NO)_2$ to the cluster.

EXAMPLE 2

Into a balloon flask under argon one introduces 1.2 g of $Na_2Fe(CO)_4$, 3/2 dioxane or 3.48 mmoles and 3.66 g of $Pd_2Cl_2(dppm)_2$ (3.48 mmoles), then cooling takes place to −78° C. and one adds 325 ml of THF previously cooled to −78° C. The suspension is then agitated. The temperature is allowed to progressively rise to 0° C. The reaction is followed by infra-red light by observing the evolution of the bands of the product in the zone of the CO vibrations. The solution is then concentrated to about 10 ml. 430 ml of pentane cooled to −78° C. are added under continued agitation. The mixture is placed for 1 hour into carbon-dioxide ice. After filtration, the solid is washed with pentane, then with distilled water and dried. It is recrystallized from dichloromethane-pentane, yielding 3 g of brown crystals (yield 75% based on Pd).

Elementary analysis: theoretical: $C=56.4\%$; $H=3.86\%$; found: $C=55.4\%$; $H=3.93\%$.

Bands in infra-red:
(solution in THF):
2024 $cm^{-1}$ (intense);
1964 $cm^{-1}$ (weak);
1939 $cm^{-1}$ (weak);
1916 $cm^{-1}$ (intense);
1868 $cm^{-1}$ (weak);
1826 $cm^{-1}$ (intense).
melting point=160° C. (decomposition)

The data from the analysis and from N.M.R. lead to attributing the formula $Pd_2Fe(CO)_4(dppm)_2$ to the cluster formed.

EXAMPLE 3

A catalyst is prepared from the cluster $Pd_2Fe(CO)_4(dppm)_2$ whose synthesis has been described in Example 2. In order to do this, there is placed into a balloon flask with solids mounted on a rotary evaporation 9 g of balls having a diameter of 2.6 mm of a silica support having a specific surface above 50 $m^2/g$ and a porous volume of above 0.7 $cm^3/g$ previously treated for one hour at 300° C. under nitrogen. The support is degasified and then with the help of a capillary there is slowly introduced a solution of 1 g of the cluster in 100 ml of THF freshly distilled on sodium and oxygen scavenged. One operates under reduced pressure of 250 mm of Hg by sprinkling the support, at such a temperature that the solvent is evaporated as the impregnation progresses. After impregnation, the impregnated support is dried and then placed into a baking tube in order to treat it thermally. A nitrogen current is allowed to pass and then the temperature is raised to 450° C. at a rate of 40° C./h. The specimen is allowed to remain 15 hours at the temperature plateau, and then a hydrogen current is introduced for one hour. After cooling, the catalyst is analyzed; the palladium content amounts to 1.9%, while the iron content amounts to 0.5%.

EXAMPLE 4

Into an autoclave of 500 ml capacity, equipped with magnetic agitation, there is introduced 7 g of orthonitrophenol (0.05 mole) which is dissolved in 100 ml of orthodichlorobenzene and 1 g of pyridine. There is added 2.75 g of the catalyst synthesized in Example 3 (thus utilizing a molar ratio of $NO_2/Pd$ of 100). After sweeping the reactor with nitrogen, there is introduced 200 bars of carbon monoxide and it is then heated to 200° C. for 3½ hours. After cooling and filtering the catalyst is fully recovered and the filtrate tested. The degree of overall conversion of the orthonitrophenol amounts to 98.4% and the selectivity in benzoxazolone-2 formed amounts to 92%.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A heteropolymetallic cluster of the formula $Pd_2(Fe)_x(CO)_4[CO(NO)_2]_y[bis(diphenylphosphine)methane]_2$ wherein x is 1 or 2; y is 0 or 1; x=2 when y=1 and x=1 when y=0.

2. The heterotetrametallic cluster of claim 1 wherein x=2 and y=1 and a melting point of 178° C. and having the following characteristic bands in infra-red spectroscopy (KBr pellet):

$1974 \text{ cm}^{-1}$ intense
$1880 \text{ cm}^{-1}$ intense
$1840 \text{ cm}^{-1}$ shoulder
$1736 \text{ cm}^{-1}$ intense
$1683 \text{ cm}^{-1}$ intense.

3. The heterotrimetallic cluster of claim 1 wherein x=1 and y=0 and a melting point of 160° C. and having the following characteristic bands in infra-red spectroscopy (in solution in tetrahydrofuran):

$2024 \text{ cm}^{-1}$ (intense)
$1964 \text{ cm}^{-1}$ (weak)
$1939 \text{ cm}^{-1}$ (weak)
$1916 \text{ cm}^{-1}$ (intense)
$1868 \text{ cm}^{-1}$ (weak)
$1826 \text{ cm}^{-1}$ (intense).

4. The method of making the clusters of claim 1, 2, or 3 comprising the step of reacting $Pd_2Cl_2[bis(diphenylphosphine)methane]$ with $M_nFe(CO)_3Z$ in which M is an alkaline metal and Z is CO (n=2) or NO (n=1).

5. The method of claim 4 wherein $M_nFe(CO)_3Z$ is selected from $KFe(CO)_3NO$ or $Na_2Fe(CO)_4$.

6. The method of claim 5 wherein the reaction takes place in the presence of solvent and at a temperature of 0° C. or below.

7. A catalyst comprising a support and liberated metallic particles formed by reduction of a cluster of claim 1, 2, or 3 after said cluster has been deposited on said support and heated.

8. The catalyst of claim 7 wherein the cluster has the formula $Pd_2(Fe)_x(CO)_4[CO(NO)_2]_y[bis(diphenylphosphine)methane]_2$ wherein x is 1 or 2, y is 0 or 1; x=2 when y=1 and x=1 when y=0.

9. The catalyst of claim 8 wherein x=2 and y=1.

10. The catalyst of claim 8 wherein x=1 and y=0.

* * * * *